United States Patent
Rha et al.

(10) Patent No.: US 12,251,216 B2
(45) Date of Patent: Mar. 18, 2025

(54) APPARATUS AND METHOD FOR HEARING ANALYSIS

(71) Applicant: RHAS TEL CO., LTD., Seoul (KR)

(72) Inventors: Hongwoon Rha, Seoul (KR); Sanghoon Kim, Seoul (KR)

(73) Assignee: RHAS TEL CO., LTD., Seoul (KR)

( * ) Notice: Subject to any disclaimer, the term of this patent is extended or adjusted under 35 U.S.C. 154(b) by 811 days.

(21) Appl. No.: 17/598,441

(22) PCT Filed: Oct. 16, 2019

(86) PCT No.: PCT/KR2019/013603
§ 371 (c)(1),
(2) Date: Sep. 27, 2021

(87) PCT Pub. No.: WO2020/197017
PCT Pub. Date: Oct. 1, 2020

(65) Prior Publication Data
US 2022/0160262 A1    May 26, 2022

(30) Foreign Application Priority Data
Mar. 25, 2019    (KR) .................. 10-2019-0033867

(51) Int. Cl.
*A61B 5/12*    (2006.01)

(52) U.S. Cl.
CPC .............. *A61B 5/128* (2013.01); *A61B 5/123* (2013.01)

(58) Field of Classification Search
CPC ........... A61B 5/12; A61B 5/121; A61B 5/123; A61B 5/125; A61B 5/128
See application file for complete search history.

(56) References Cited

U.S. PATENT DOCUMENTS

2006/0167335 A1    7/2006    Park et al.
2009/0124850 A1    5/2009    Moore et al.
(Continued)

FOREIGN PATENT DOCUMENTS

KR    10-0647310 B1    11/2006
KR    20140145394 A  *  12/2014
(Continued)

OTHER PUBLICATIONS

Jan. 23, 2020 Search Report issued in International Patent Application No. PCT/KR2019/013603.
(Continued)

*Primary Examiner* — Daniel L Cerioni
*Assistant Examiner* — Abel Seifu Abegaz
(74) *Attorney, Agent, or Firm* — Oliff PLC (57) ABSTRACT

An apparatus and method for hearing analysis including a frequency setting part for setting a predetermined frequency at which there is a possibility of tinnitus of the subject; a signal generation part generates a pure tone signal of the set frequency and increase or decrease the level of the generated pure tone signal, and generates a complex tone signal including the frequency of the pure tone signal and increase or decrease a level of the generated complex tone signal; and a hearing analysis part to analyze hearing by using a pure tone recognition information and a complex tone recognition information of the subject obtained in reaction to the pure tone signal and the complex tone signal generated by the signal generation part. As a result, the apparatus and method can accurately determine the tinnitus region and also provide information from which point of the sound path the tinnitus originates.

13 Claims, 4 Drawing Sheets (56) References Cited

U.S. PATENT DOCUMENTS

| | | | | |
|---|---|---|---|---|
| 2011/0263926 A1* | 10/2011 | Kwak | .................... | H04R 25/50 |
| | | | | 600/28 |
| 2015/0003650 A1* | 1/2015 | Drexler | ................ | A61B 5/4836 |
| | | | | 381/312 |
| 2015/0073296 A1* | 3/2015 | Zeng | ...................... | A61B 5/128 |
| | | | | 600/559 |
| 2020/0129760 A1* | 4/2020 | Baker | .................. | H04R 1/1016 |

FOREIGN PATENT DOCUMENTS

| | | |
|---|---|---|
| KR | 10-1517957 B1 | 5/2015 |
| KR | 10-2015-0129662 A | 11/2015 |
| KR | 10-2016-0033706 A | 3/2016 |
| WO | 2020/111512 A1 | 6/2020 |

OTHER PUBLICATIONS

Sep. 28, 2021 International Preliminary Report on Patentability issued in International Patent Application No. PCT/KR2019/013603.

\* cited by examiner

APPARATUS AND METHOD FOR HEARING ANALYSIS

TECHNICAL FIELD

The present disclosure relates to an apparatus and a method for hearing analysis, and more particularly, to an apparatus and a method for analyzing a human hearing by comparing auditory reactions to a plurality of signals associated with the same frequency.

BACKGROUND ART

Sound is transmitted as a wave energy from an ear canal to an eardrum of an ear region; the wave energy is converted into a vibration energy at the eardrum and the vibration energy is then transmitted through auditory ossicles to an oval window; the vibration energy is converted into a fluid energy at the oval window and the fluid energy is then transmitted to hair cells of a cochlea; and sound information is then transmitted to an auditory nerve through a chemical reaction of inner hair cells among the hair cells; The process of transmitting sound information to the auditory cortex of the cerebrum through the central nerve consists of synaptic activity of each neuron. Through this process, the brain can finally recognize sound in association with the frontal lobe of the cerebral cortex.

Meanwhile, it is generally called tinnitus to recognize the sound in the human ear even when there is no sound from the outside due to changes in the human body. The process of measuring such tinnitus is disclosed in Korea Patent Publication No. 10-0647310. In Korean Patent Publication No. 10-0647310, a pure tone signal is generated for some frequencies within an audible frequency range, and when the sound suddenly sounds loud while the pure tone signal is increasing, a point where the sound suddenly sounds loud is determined to be the point of tinnitus. However, this tinnitus test method has a problem in that it is difficult to accurately determine the tinnitus region and to know from which point of the sound path the tinnitus originates.

DISCLOSURE OF INVENTION

Technical Problem

In order to solve the above problems, an aspect of the present disclosure is to provide an apparatus and a method for analyzing a human hearing by comparing auditory reactions to a plurality of signals associated with the same frequency.

Solution to Problem

According to one embodiment of the invention, an apparatus of a hearing analysis may comprise: a frequency setting part configured to set a predetermined frequency at which there is a possibility of tinnitus of a subject; a signal generation part configured to generate a pure tone signal of the set frequency and increase or decrease a level of the generated pure tone signal, and generate a complex tone signal including the frequency of the pure tone signal and increase or decrease a level of the generated complex tone signal; and a hearing analysis part configured to analyze a hearing of the subject by using a pure tone recognition information and a complex tone recognition information of the subject obtained in reaction to the pure tone signal and the complex tone signal generated by the signal generation part.

According to a further embodiment of the invention, the pure tone signal and the complex tone signal generated by the signal generation part may be output at the same level when the pure tone recognition information and the complex tone recognition information are obtained.

According to a further embodiment of the invention, the frequency setting part may set a frequency band range at which there is a possibility of tinnitus, and the signal generation part may output the pure tone signal and the complex tone signal in sequence for a plurality of frequencies within the frequency band range.

According to a further embodiment of the invention, the complex tone signal may be a real harmonic acoustic sound signal generated by combining the frequency of the pure tone signal with harmonic frequencies thereof.

According to a further embodiment of the invention, the real harmonic acoustic sound signal may have a saw tooth triangular waveform or an isosceles triangular waveform.

According to a further embodiment of the invention, the signal generation part may generate a brain wave signal, synthesize the generated brain wave signal with the pure tone signal or the real harmonic acoustic sound signal, and provide the synthesized brain wave.

According to a further embodiment of the invention, the signal generation part may select and output either the pure tone signal or the real harmonic acoustic sound signal.

According to a further embodiment of the invention, the hearing analysis part may analyze the hearing of the subject by using at least one of a volume difference, a frequency change and a sound tremor, between the pure tone recognition information and the complex tone recognition information of the subject.

According to a further embodiment of the invention, the apparatus may further comprise an information storage part configured to store the pure tone recognition information and the complex tone recognition information, and wherein the hearing analysis part is configured to divide an audible frequency band into a hearing normal region, a hearing attenuation region, a tinnitus potential region, and a tinnitus occurrence region and determine the hearing normal region, the hearing attenuation region, the tinnitus potential region, and the tinnitus occurrence region within the audible frequency band by using the pure tone recognition information and the complex tone recognition information.

According to another embodiment of the invention, a method for a hearing analysis may comprise: setting a predetermined frequency at which there is a possibility of tinnitus of a subject; generating a pure tone signal of the set frequency and increasing or decreasing a level of the generated pure tone signal; generating a complex tone signal comprising the frequency of the pure tone signal; and analyzing a hearing of the subject by using a pure tone recognition information and a complex tone recognition information of the subject obtained in reaction to the pure tone signal and the complex tone signal.

Advantageous Effects of Invention

According to the features described above, the present disclosure can not only accurately determine a tinnitus region but also provide information from which point of the sound path the tinnitus originates.

In addition, the present disclosure can compare cognitive informations to subdivide a hearing normal region, a hearing attenuation region, a tinnitus potential region, and a tinnitus occurrence region within the audible frequency band.

In addition, the present disclosure is capable of auditory evaluation related to hair cells and synapses to distinguish between a conductive tinnitus and a neuromonics tinnitus, thus maximizing the effect of hearing improvement through medical treatment.

BRIEF DESCRIPTION OF DRAWINGS

The above and other aspects, features and advantages of the present disclosure will be more apparent from the following detailed description taken in conjunction with the accompanying drawings, in which:

FIG. 5 illustrates a hearing analysis part illustrated in FIG. 1 in detail.

FIG. 6 is a flowchart illustrating a hearing analysis method according to another embodiment of the present disclosure.

FIG. 7 is a diagram illustrating a system including a hearing analysis apparatus and a hearing improvement apparatus, according to other embodiment of the present disclosure.

MODE FOR THE INVENTION

Hereinafter, preferable embodiments of a hearing analysis apparatus and method according to the present disclosure will be described with reference to the accompanying drawings. For reference, in the following description, the terms referring to elements of the present disclosure are set in consideration of the functions of the elements, and thus should not be construed to limit the technical elements of the present disclosure.

Figure 1:
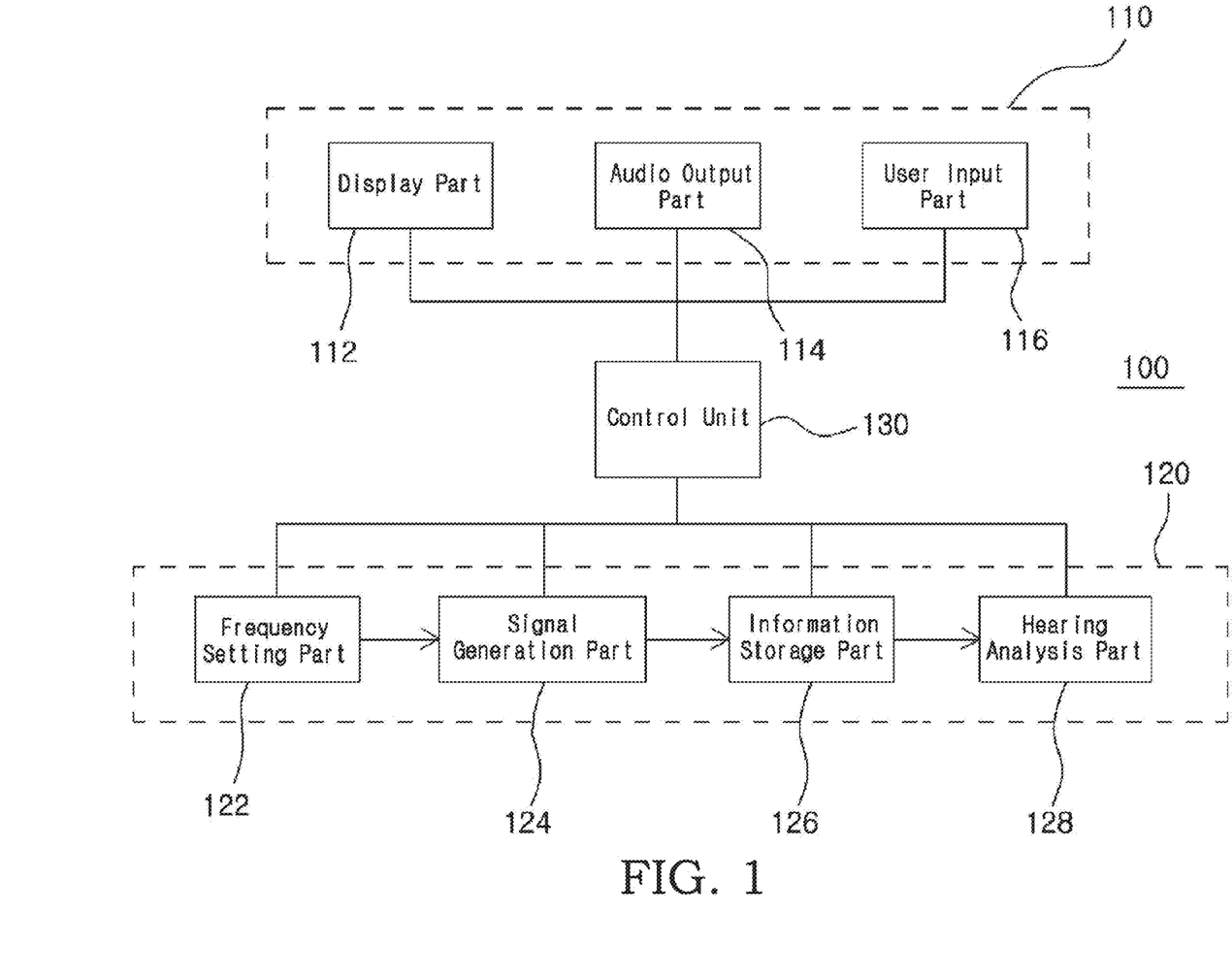
FIG. 1 is a schematic block diagram of a hearing analysis apparatus according to an embodiment of the present disclosure.
Figure 2:
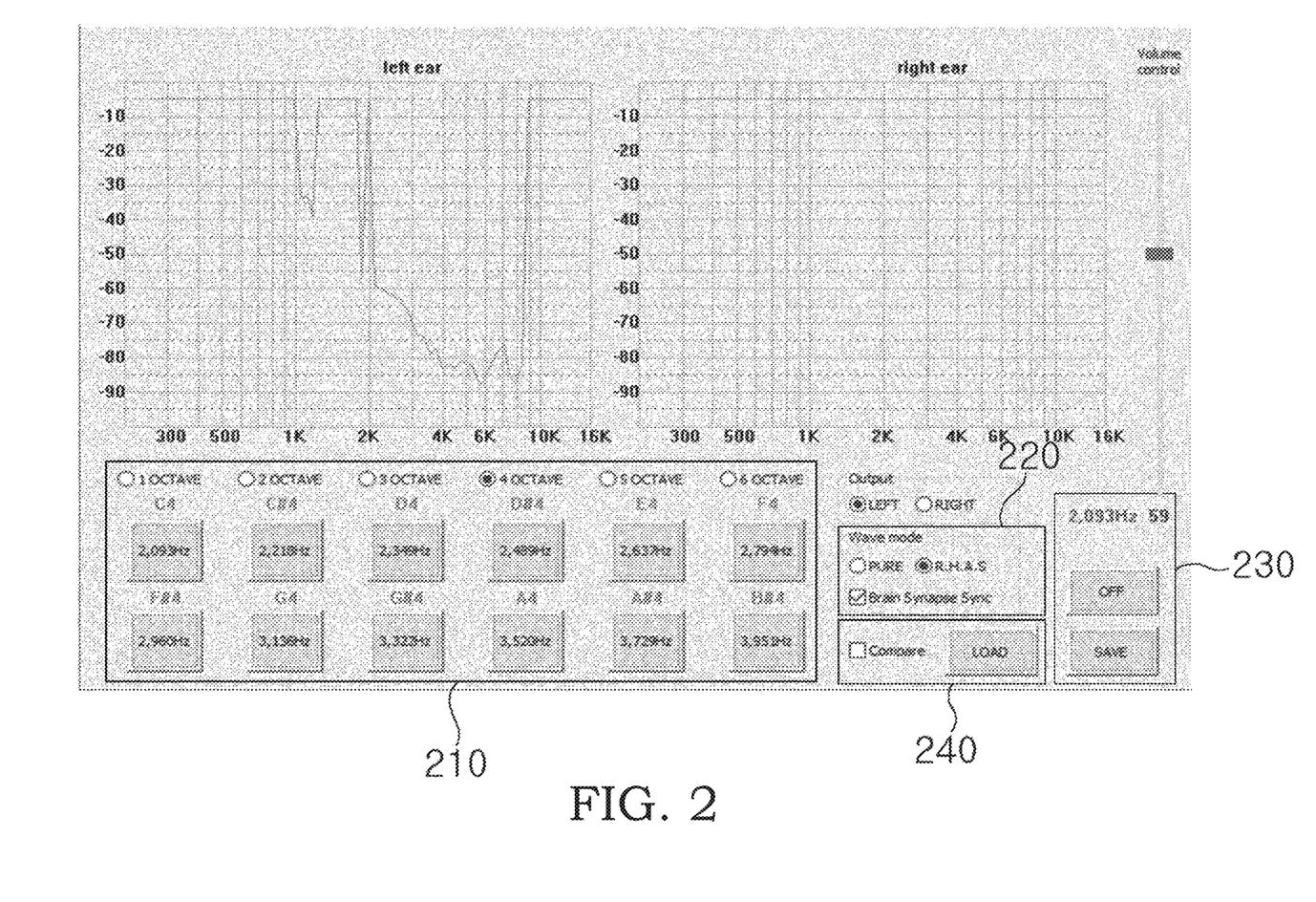
FIG. 2 illustrates an example of a screen displayed on the display part illustrated in FIG. 1.
Figure 3:
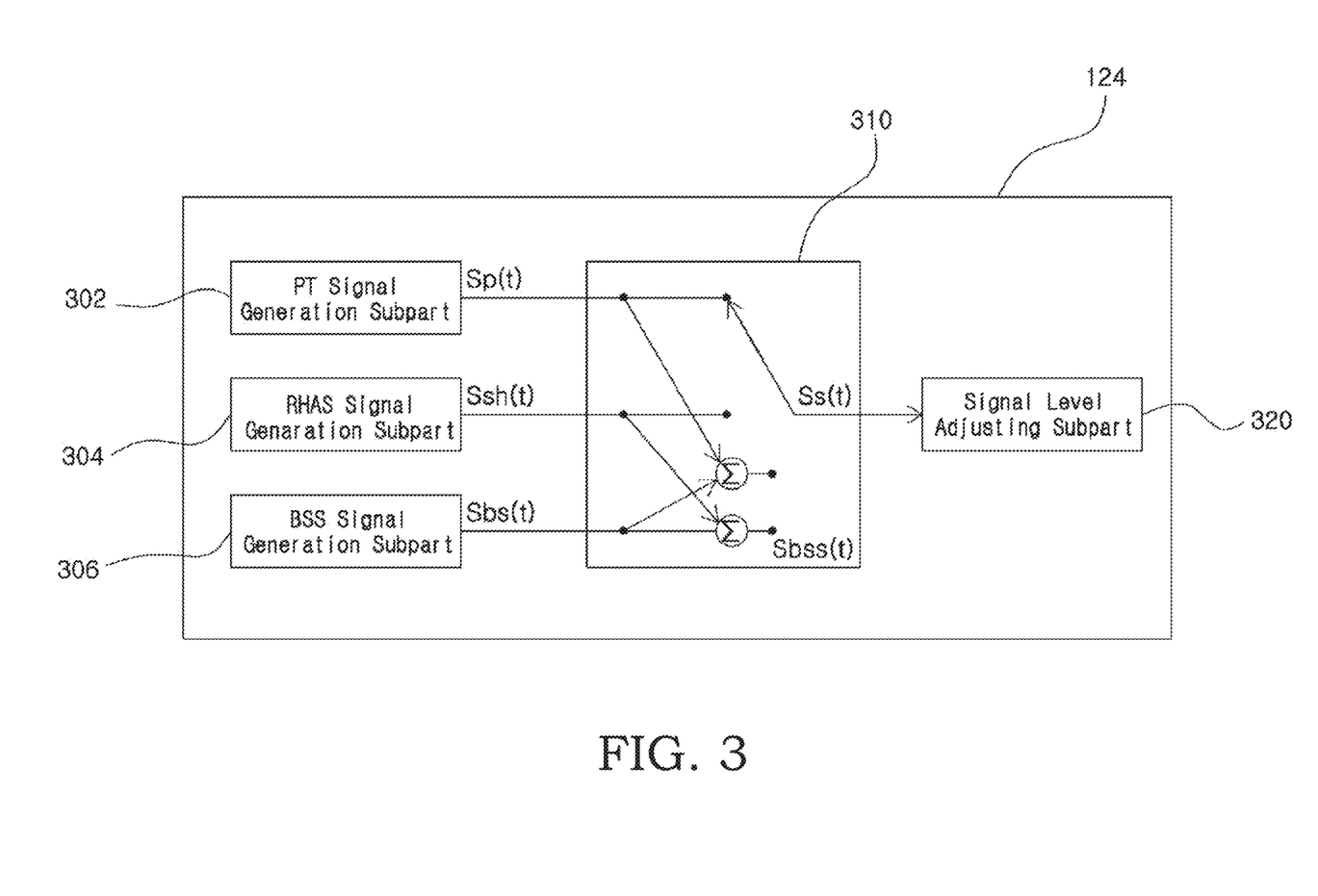
FIG. 3 illustrates a signal generation part illustrated in FIG. 1 in detail.
Figure 4:
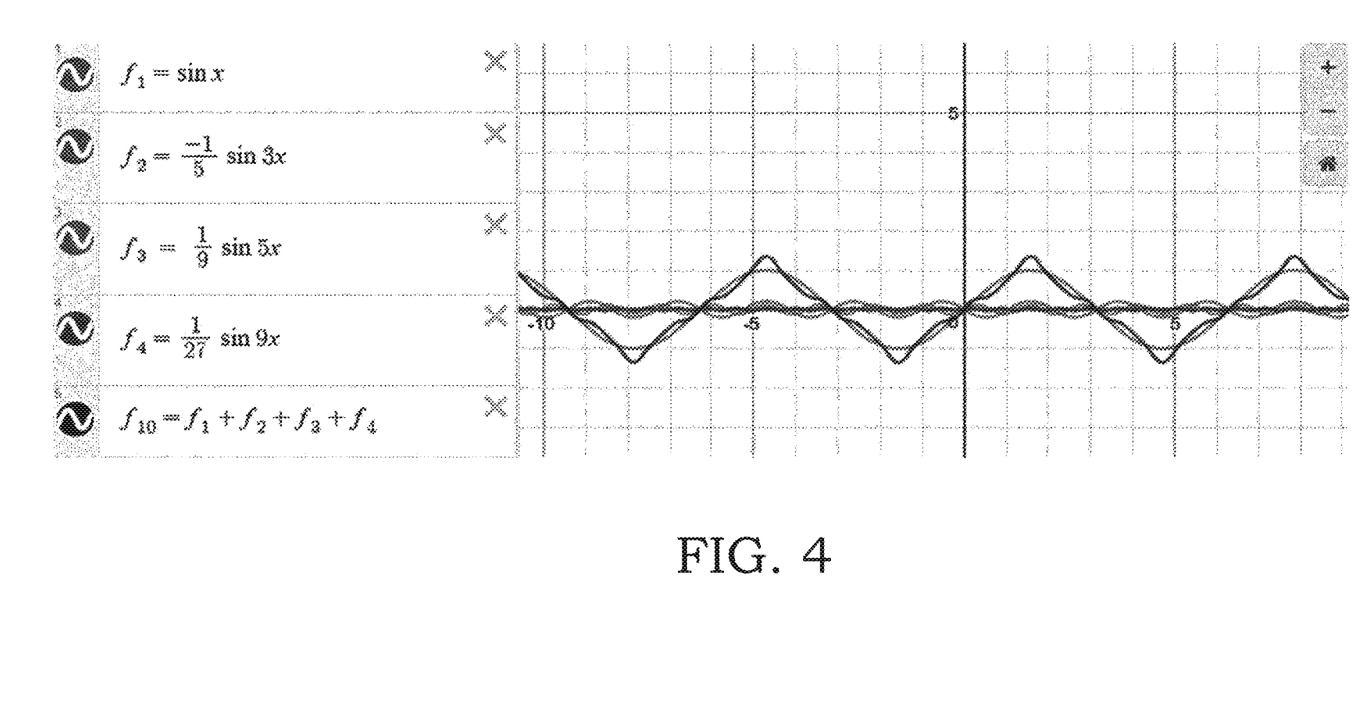
FIG. 4 illustrates an example of a real harmonic acoustic sound signal generated by the signal generation part of FIG. 3.

FIG. 1 is a schematic block diagram of a hearing analysis apparatus according to an embodiment of the present disclosure, FIG. 2 illustrates an example of a screen displayed on the display part illustrated in FIG. 1, FIG. 3 illustrates a signal generation part illustrated in FIG. 1 in detail, FIG. 4 illustrates an example of a real harmonic acoustic sound signal generated by the signal generation part of FIG. 3, and FIG. 5 illustrates a hearing analysis part illustrated in FIG. 1 in detail.

The hearing analysis apparatus 100 includes a user interface unit 110, a hearing analysis unit 120, and a control unit 130, as shown in FIG. 1.

The user interface unit 110 is configured to interface with a user, that is, an inspector or a subject, and includes a display part 112, an audio output part 114, and a user input part 116.

The display part 112 may display a screen illustrated in FIG. 2. As illustrated in FIG. 2, the screen displayed on the display part 112 may be divided into an area 210 associated with a frequency setting part 122, an area 220 associated with a signal generation part 124, an area 230 associated with an information storage part 126, and an area 240 associated with a hearing analysis part 128.

The audio output part 114 outputs a signal provided from the hearing analysis unit 120 and may be, for example, earphones or headphones.

The user input part 116 is configured to input user information in reaction to the sound of the audio output part 114 and may be, for example, a keyboard. Meanwhile, when hearing is measured and analyzed manually, the user may select by means of the user input part 116, items of the area 210 associated with the frequency setting part 122 and the area 220 associated with the signal generation part 124 illustrated in FIG. 2.

The hearing analysis unit 120 includes the frequency setting part 122, the signal generation part 124, the information storage part 126, and the hearing analysis part 128.

The frequency setting part 122 sets a predetermined frequency at which there is a possibility of tinnitus of the subject on the basis of the hearing measurement by means of a pure tone signal. For example, the frequency setting part 122 may set a frequency band range at which there is a possibility of tinnitus within the audible frequency range of humans on the basis of results of the hearing measurement by means of a pure tone signal or may set a frequency selected by the user by means of the user input part 116 to the predetermined frequency at which there is the possibility of tinnitus.

The frequency setting part 122 may include, for example, six octave regions as shown in [Table 1].

TABLE 1

| Octave Number | Frequency Range |
| --- | --- |
| 1 OCTAVE | 250 Hz~500 Hz |
| 2 OCTAVE | 500 Hz~1 kHz |
| 3 OCTAVE | 1 kHz~2 kHz |
| 4 OCTAVE | 2 kHz~4 kHz |
| 5 OCTAVE | 4 kHz~8 kHz |
| 6 OCTAVE | 8 kHz~16 kHz |

Each octave can use 12 frequencies on the basis of a piano scale.

FIG. 2 shows these six octaves, of which twelve frequencies associated with the fourth octave are shown.

The signal generation part 124 generates a pure tone signal of the frequency set by the frequency setting part 122 and generates a complex tone signal including the frequency of the pure tone signal. The signal generation part 124 may adjust and output a level of the generated pure tone signal or the complex tone signal.

The signal generation part 124 may include a pure tone (PT) signal generation subpart 302, a real harmonic acoustic sound (RHAS) signal generation subpart 304, and a brain synapse sync (BSS) signal generation subpart 306, a signal selection subpart 310, and a signal level adjusting subpart 320.

The pure tone signal generation subpart 302 generates and outputs a pure tone signal matched to the frequency set by the frequency setting part 122. Here, the pure tone signal $Sp(t)$ is a signal having $\sin(t)$ value: $(Sp(t)=\sin(t))$.

The RHAS signal generation subpart 304 generates a RHAS signal composed of harmonic waves including the frequency of the pure tone signal. Here, the harmonic signal $Srh(t)$ is composed of the sum of harmonic components having the integer multiple of the reference frequency of the following form: $Srh(t)=\Sigma[A*F(1)+B*F(2)+C*F(3)+D*F(4)+ \ldots +N*F(n)]$. This signal can be classified into $Srho(t)$, $Srhe(t)$, and $Srhoe(t)$, where $Srho(t)=\Sigma[B*F(2)+D*F(4)+F*F(6)+ \ldots +N*F(2n)]$ (even harmonic components);

Srhe(t)=Σ[A*F(1)+C*F(3)+E*F(5)+ . . . +N*F(n)] (odd harmonic component); and Srhoe(t)=Σ[A*F(1)+B*F(2)+C*F(3)+D*F(4)+ . . . +N*F(n)] (even/odd synthesis harmonic components). If C*F(3) is a reference frequency component, the values of constants A, B, D, . . . N (excluding the constant C) have values smaller than one-third (⅓) of the value of the constant C. All constant values can have positive/negative (+/−) values depending on conditions. If F(3) is the reference frequency, F(4) is twice (2) the harmonic component, and F(2) is one-second (½) of the harmonic component.

Meanwhile, if the values of the coefficients of even harmonic components are all positive (+) values, for example, Srhe(t)=sin(x)+⅕ sin(2x)+⅑ sin(4x)+1/27 sin(8x), then the RHAS signal will have a square waveform. However, if the values of the coefficients are a mixture of positive (+) and negative (−) values, for example Srhe(t)=sin(x)+(−⅕)sin(2x)+1/11 sin(4x)+1/21 sin(6x) or Srhe(t)=sin(x)+⅕ sin(2x)+(−1/15)sin(4x)+1/21 sin(6x), then the RHAS signal will have a saw tooth triangular waveform.

Further, if the values of the coefficients of the odd harmonic components are all positive (+) values, for example, Srho(t)=sin(x)+⅕ sin(3x)+⅑ sin(5x)+1/13 sin(7x), then the RHAS signal will have a waveform close to a square wave. However, if the values of the coefficients are a mixture of positive (+) and negative (−) values, Srho(t)=sin(x)+(−⅕)sin(3x)+⅑ sin(5x)+1/27 sin(9x), then the RHAS signal will have an isosceles triangle waveform. The above RHAS signal Srho(t) composed of sin(x)+(−⅕)sin(3x)+⅑ sin(5x)+1/27 sin(9x) is shown in FIG. 4.

These various RHAS signals may be used for hearing analysis. However, the present inventors have found that the isosceles triangular waveform having the waveform closest to the pure sound signal waveform among various RHAS signals is most suitable for distinguishing the degree of sound volume difference, the degree of frequency change or the degree of sound tremor.

The BSS signal generation subpart 306 generates a signal in tune with a brain wave. The BSS signal is divided into delta wave, theta wave, alpha wave, SMR wave, beta wave, and gamma wave as an active frequency according to the activity of the brain wave. Among them, the signal in the region from the alpha wave to the gamma wave may be output as a BSS signal Sbs(t). Therefore, the Sbs(t) signal has a distribution of 8 Hz to 200 Hz, which corresponds to the range of 8 Hz to 30 Hz from alpha wave to the beta wave of the brain wave, and the range of 50 Hz to 200 Hz related to 5 msec to 20 msec period which is the real processing time for executing the byte command of the human body.

The signal selection subpart 310 receives the PT signal Sp(t), the RHAS signal Srh(t) and the BSS signal Sbs(t). The BSS signal Sbs(t) is converted into a synthesized BSS signal Sbss(t) where this conversion process is expressed by Sbss(t)=Sbs(t)*Sp(t) or Sbs(t)*Srh(t). As a result, the signal selection subpart 310 may select any one of the PT signal Sp(t), the RHAS signal Srh(t), and the synthesized BSS signal Sbss(t) to output it as a selection signal Ss(t).

In addition, the signal level adjusting subpart 320 adjusts a level of the selection signal Ss(t) output from the signal selection subpart 310. The level-adjusted selection signal Ss(t) is provided to the audio output part 114, and the audio output part 114 provides the sound to the subject.

The information storage part 126 stores informations input by the subject in reaction to the sound of the selection signal Ss(t) output from the signal generation part 124. For example, the information storage part 126 may store a pure tone recognition information obtained in reaction to the pure tone signal output from the signal generation part 124, a RHAS recognition information obtained in reaction to the RHAS signal output from the signal generation part 124, and a synthetic BSS recognition information obtained in reaction to the synthesized BSS signal output from the signal generation part 124. In addition, these cognitive informations may be obtained for each of the left ear and the right ear.

The hearing analysis part 128 analyzes hearing ability of the subject by using these cognitive informations of the subject obtained in reaction to the pure tone signal and the complex tone signal generated by the signal generation part 124.

As shown in FIG. 5, the hearing analysis part 128 may include a comparison analysis subpart 502 and a hearing condition determination subpart 504.

The comparison analysis subpart 502 may compare and analyze the pure tone recognition information with the RHAS recognition information and/or the synthesized BSS recognition information, stored in the information storage part 126. That is, the RHAS recognition information may be compared and analyzed on the basis of pure tone recognition information and the synthetic BSS recognition information may be compared and analyzed on the basis of the pure tone recognition information. The comparison analysis subpart 502 may comprehensively analyze displacement differences, for example, a volume difference, a frequency change and a sound tremor, on the basis of the recognition informations for each frequency, and may display these results in the frequency band.

The hearing state determination subpart 504 may determine a hearing state, for example, a hearing normal region, a hearing attenuation region, a tinnitus potential region, and a tinnitus occurrence region by using the result analyzed by the comparison analysis subpart 502. For example, when the pure tone signal is compared with the complex tone signal, the normal hearing state corresponds to the case where the sounds of two signals sound almost the same without the volume difference; the attenuated hearing state corresponds to the case where the sounds of two signals sound almost the same with respect to the frequency but the complex tone signal has a lower volume than the pure tone signal(i.e., sensory problem); the tinnitus potential state corresponds to the case where the sounds of two signals sound different from each other with respect to the frequency(i.e., nerve problem); and the tinnitus occurrence state corresponds to the case where the sounds of two signals sound different from each other respect to the frequency and the sound of the complex tone signal is trembling(i.e., unbalance between hair cell and synapse).

The present inventors have found that the hearing attenuation occurs because there is a problem with the reaction of some of the hair cells; the tinnitus potential occurs because of deterioration of the hair cells; and the tinnitus occurs because of imbalances of neuronal synapses as well as deterioration of the hair cells. That is, when a user recognizes that the sounds of the pure tone signal and the complex tone signal are almost the same with respect to the frequency but the complex tone signal has a lower volume than the pure tone signal, it is determined that the user has a problem with the reaction of some of the hair cells; when the user recognizes that the sounds of the pure tone signal and the complex tone signal have different frequencies and volumes change differently, it is determined that the user has a problem with deterioration of the hair cells; and when the user recognizes that the sounds of the pure tone signal and the complex tone signal have different frequencies and the sound of the complex tone signal is trembling, it is determined that the user has a problem with imbalances of neuronal synapses as well as deterioration of the hair cells.

The control unit 130 may change a display of the display part 112 according to the informations input from the user input part 116, control the frequency setting part 122 and the signal generation part 124, and store the cognition informations in the information storage part 126.

FIG. 6 is a flowchart illustrating a hearing analysis method according to another embodiment of the present disclosure.

First, the hearing analysis apparatus 100 performs a hearing test of a subject (S602). In general, the hearing test is performed by outputting a pure tone signal while sequentially increasing frequencies from 1 OCTAVE to 6 OCTAVE on the screen in FIG. 2. The subject reacts at the point where the subject recognizes the sound while the pure tone level is increasing, and a test information is stored in the information storage unit 126.

The frequency setting part 122 sets a frequency band range at which there is a possibility of tinnitus within an audible frequency range on the basis of results of the hearing test by means of the pure tone signal (S604). A plurality of frequencies may be included in the set frequency band range. In this case, first, a frequency to be measured among the plurality of frequencies, for example, the lowest frequency, is set (S606).

The signal generation part 124 generates and outputs the pure tone signal that matches with the frequency set by the frequency setting part 122 and increases a level of the output pure tone signal (S608). The pure tone signal is output through the audio output part 114, and the subject responds by means of the user input part 116 when the subject recognizes a sound. Accordingly, the information storage part 126 stores a pure tone recognition information obtained in reaction to the pure tone signal output from the signal generation part 124 (S610).

The signal generation part 124 may generate and output an RHAS signal that matches with the frequency set by the frequency setting part 122 on the basis of the pure tone recognition information obtained in reaction to the pure tone signal (S612). In this case, it is preferable that the pure tone signal and the RHAS signal maintain the same level for comparison and analysis. The RHAS signal is output through the audio output part 114, and the subject responds by means of the user input part 116 when the subject recognizes a sound. Accordingly, the information storage part 126 stores RHAS recognition information obtained in reaction to the RHAS signal output from the signal generation part 124 (S614). In this case, the information storage part 126 may store not only the RHAS recognition level but also the frequency change and/or the sound tremor, by the inspector or the subject. In checking the frequency change and/or the sound tremor, the signal generation part 124 may repeatedly play the pure tone signal and the RHAS signal.

The signal generation part 124 may continuously synthesize a BSS signal to the pure tone signal or the RHAS signal matched to the frequency set by the frequency setting part 122 and output the synthesized BSS signal (S616). The synthesized BSS signal is output through the audio output part 114, and the subject responds by means of the user input part 116 when the subject recognizes the sound. Accordingly, the information storage part 126 stores a synthetic BSS recognition information obtained in reaction to the synthesized BSS signal output from the signal generation part 124 (S618). In this case, the information storage part 126 may store not only the synthesized BSS recognition level but also the frequency change and/or the sound tremor, by the inspector or the subject. In checking the frequency change and/or the sound tremor, the signal generation part 124 may repeatedly play the pure tone signal and the synthesized BSS signal, and may obtain more informations, such as whether the frequency change and/or the sound tremor is severer than in the RHAS signal.

When all recognition informations are input for a set frequency among the plurality of frequencies, the hearing analysis apparatus 100 checks whether the measurement has completed for all frequencies (S620). If there is a frequency for which the measurement has not yet been completed among the plurality of frequencies, next frequency, for example, a second frequency is set (S622).

When the measurement has completed for all of the plurality of frequencies, the hearing analysis part 128 first compares the pure tone recognition information with the RHAS recognition information stored in the information storage part 126 (S624) to analyze how much level difference occurred for each frequency and whether there was the frequency change and/or the sound tremor. The hearing analysis part 128 also compares the pure tone recognition information or the RHAS recognition information with the synthetic BSS recognition information stored in the information storage part 126 (S626) to analyze how much level difference occurred for each frequency and whether there was the frequency change and/or the sound tremor. These analyses can be used for determining the effect of neural synapses on tinnitus. Further, the control unit 130 may display the result of the comparative analysis on the frequency display area of the display screen.

The hearing analysis part 128 determines a hearing state by dividing a hearing normal region, a hearing attenuation region, a tinnitus potential region, and a tinnitus occurrence region within the audible frequency band by using the result of the comparative analysis above (S628). In addition, the control unit 130 may display the determined hearing condition on the display screen.

In FIG. 6, in relation to the frequency band range at which there is a possibility of tinnitus, it is illustrated that the hearing test of the subject is first performed by using pure sound, and then the frequency band range at which there is a possibility of tinnitus is set on the basis of the result. However, since the object of the present disclosure can be achieved by comparative analysis of pure tone recognition information and RHAS recognition information or synthesized BSS recognition information, such a hearing test that uses only a pure tone is not necessarily required.

FIG. 7 is a diagram illustrating a system including a hearing analysis apparatus and a hearing improvement apparatus, according to other embodiment of the present disclosure.

As shown in FIG. 7, the frequency-related cognitive information analyzed by the hearing analysis apparatus 100 may be provided to the hearing improvement apparatus 700.

The hearing improvement apparatus 700 is described in the Korean Patent Application No. 2018-0149990 filed by the applicant as a perceptual ability improving device, the patent application should be considered to be included herein.

The embodiments of the present disclosure are merely examples of the technical idea of the present disclosure, and the scope of the present disclosure should be interpreted based on the claims. Further, it can be understood by those skilled in the art that various modifications and changes can be made without departing from the essential features of the present disclosure and that all technical ideas within the equivalent range to the present disclosure should be construed as being included in the scope of the present disclosure.

The invention claimed is:

1. An apparatus of a hearing analysis, the apparatus comprising:
   a frequency setting part configured to set a predetermined frequency at which there is a possibility of tinnitus of a subject;
   a signal generation part configured to generate a pure tone signal of the set frequency and increase or decrease a level of the generated pure tone signal, and generate a complex tone signal including the frequency of the pure tone signal and increase or decrease a level of the generated complex tone signal;
   an audio output part configured to output sound of the pure tone signal and the complex tone signal generated by the signal generation part;
   a user input part configured to input a subject's response to the sound;
   an information storage part configured to store a pure tone recognition information and a complex tone recognition information generated based on the response; and
   a hearing analysis part configured to analyze a hearing of the subject by using the pure tone recognition information and the complex tone recognition information of the subject stored in the information storage part;
   wherein the complex tone signal is a real harmonic acoustic sound signal generated by combining the frequency of the pure tone signal with harmonic frequencies thereof, and
   wherein the real harmonic acoustic sound signal has a saw tooth triangular waveform or an isosceles triangular waveform.

2. The apparatus of claim 1, wherein the pure tone signal and the complex tone signal generated by the signal generation part are output at the same level when the pure tone recognition information and the complex tone recognition information are obtained.

3. The apparatus of claim 2, wherein the frequency setting part sets a frequency band range at which there is a possibility of tinnitus, and the signal generation part outputs the pure tone signal and the complex tone signal in sequence for a plurality of frequencies within the frequency band range.

4. The apparatus of claim 1, wherein the signal generation part generates a brain wave signal which is in tune with a brain wave of the subject, synthesizes the generated brain wave signal with the pure tone signal or the real harmonic acoustic sound signal, and provides the synthesized brain wave signal,
   wherein the brain wave signal has frequency ranges between 8 Hz and 30 Hz and between 50 Hz and 200 Hz.

5. The apparatus of claim 1, wherein the signal generation part is configured to select and output either the pure tone signal or the real harmonic acoustic sound signal.

6. The apparatus of claim 5, wherein the hearing analysis part is configured to analyze the hearing of the subject by using at least one of a volume difference, a frequency change and a sound tremor, between the pure tone recognition information and the complex tone recognition information of the subject.

7. The apparatus of claim 6, further comprising an information storage part configured to store the pure tone recognition information and the complex tone recognition information, and wherein the hearing analysis part is configured to divide an audible frequency band into a hearing normal region, a hearing attenuation region, a tinnitus potential region, and a tinnitus occurrence region and determine the hearing normal region, the hearing attenuation region, the tinnitus potential region, and the tinnitus occurrence region within the audible frequency band by using the pure tone recognition information and the complex tone recognition information.

8. A method for a hearing analysis, the method comprising:
   setting a predetermined frequency at which there is a possibility of tinnitus of a subject;
   generating a pure tone signal of the set frequency and increasing or decreasing a level of the generated pure tone signal;
   generating a complex tone signal comprising the frequency of the pure tone signal;
   outputting sound of the pure tone signal and the complex tone signal generated by the signal generation part;
   when a subject's response to the sound is input, storing a pure tone recognition information and a complex tone recognition information generated based on the response; and
   analyzing a hearing of the subject by using the stored pure tone recognition information and complex tone recognition information of the subject;
   wherein, the complex tone signal is a real harmonic acoustic sound signal generated by combining the frequency of the pure tone signal with harmonic frequencies thereof, and
   wherein the real harmonic acoustic sound signal has a saw tooth triangular waveform or an isosceles triangular waveform.

9. The method of claim 8, wherein the pure tone signal and the complex tone signal are output at the same level when the pure tone recognition information and the complex tone recognition information are obtained.

10. The method of claim 9, further comprising setting a frequency band range at which there is a possibility of tinnitus of the subject, wherein the setting the predetermined frequency includes setting a plurality of frequencies of the frequency band range,
    and the pure tone signal and the complex tone signal are sequentially output for the plurality of frequencies within the frequency band range.

11. The method of claim 8, further comprising: generating a brain wave signal which is in tune with a brain wave of the subject; synthesizing the generated brain wave signal with the pure tone signal or the real harmonic acoustic sound signal; and providing the synthesized brain wave signal,
    wherein the brain wave signal has frequency ranges between 8 Hz and 30 Hz and between 50 Hz and 200 Hz.

12. The method of claim 8, wherein the analyzing the hearing of the subject comprises analyzing the hearing of the subject by using at least one of a volume difference, a frequency change and a sound tremor, between the pure tone recognition information and the complex tone recognition information of the subject.

13. The method of claim 12, wherein the analyzing of the hearing of the subject includes dividing an audible frequency band into a hearing normal region, a hearing attenuation region, a tinnitus potential region, and a tinnitus occurrence region and determining the hearing normal region, the hearing attenuation region, the tinnitus potential region, and the tinnitus occurrence region within the audible frequency band by using the pure tone recognition information and the complex tone recognition information.

\* \* \* \* \*